(12) United States Patent
Reniers

(10) Patent No.: US 10,677,910 B2
(45) Date of Patent: Jun. 9, 2020

(54) SYSTEM FOR LOCATING AN OBJECT USING AN ANTENNA ARRAY WITH PARTIALLY OVERLAPPING COILS

(71) Applicant: Technische Universiteit Eindhoven, Eindhoven (NL)

(72) Inventor: Adrianus C. F. Reniers, Valkenswaard (NL)

(73) Assignee: Technische Universiteit Eindhoven, Eindhoven (NL)

( * ) Notice: Subject to any disclaimer, the term of this patent is extended or adjusted under 35 U.S.C. 154(b) by 573 days.

(21) Appl. No.: 15/036,116

(22) PCT Filed: Nov. 13, 2014

(86) PCT No.: PCT/EP2014/074461
§ 371 (c)(1),
(2) Date: May 12, 2016

(87) PCT Pub. No.: WO2015/071347
PCT Pub. Date: May 21, 2015

(65) Prior Publication Data
US 2016/0282461 A1    Sep. 29, 2016

Related U.S. Application Data

(60) Provisional application No. 61/904,111, filed on Nov. 14, 2013.

(51) Int. Cl.
*G01S 13/75*  (2006.01)
*A61B 34/20*  (2016.01)
(Continued)

(52) U.S. Cl.
CPC .............. *G01S 13/75* (2013.01); *A61B 8/445* (2013.01); *A61B 90/98* (2016.02); *G01S 13/82* (2013.01);
(Continued)

(58) Field of Classification Search
CPC .. G01S 13/74–84; H01Q 1/2208–2275; H01Q 7/00; H01Q 5/40–49;
(Continued)

(56) References Cited

U.S. PATENT DOCUMENTS 7,439,862 B2 * 10/2008 Quan ................. G06K 7/10128
340/10.3
7,612,675 B2 * 11/2009 Miller ....................... A63F 1/06
340/10.4

(Continued)

FOREIGN PATENT DOCUMENTS

DE      2437464      2/1976
EP      0172445      11/1989
(Continued)

*Primary Examiner* — Matthew M Barker
(74) *Attorney, Agent, or Firm* — Lumen Patent Firm

(57) ABSTRACT

A system is provided for wirelessly locating objects. The system has a transceiver unit with an antenna array of two partially overlapping coils, which is used in combination with a passive electromagnetic reflector to track or locate the objects. The system is tuned to reflect and receive higher order harmonics of a transmitted signal frequency. The system is reliable in a highly reflective environment with no placement error detection due to reflections. A relatively large distance can be bridged with a minimum power and a small sensitive area to detect the coils, which increase the accuracy to determine the location of the electromagnetic reflector.

5 Claims, 5 Drawing Sheets

(51) Int. Cl.
| | |
|---|---|
| *A61B 90/98* | (2016.01) |
| *G01S 13/82* | (2006.01) |
| *H01Q 1/22* | (2006.01) |
| *H01Q 7/00* | (2006.01) |
| *H01Q 5/40* | (2015.01) |
| *A61B 8/00* | (2006.01) |
| *G06K 7/10* | (2006.01) |
| *G06K 19/067* | (2006.01) |
| *A61B 8/12* | (2006.01) |
| *A61B 5/00* | (2006.01) |

(52) U.S. Cl.
CPC ............. *H01Q 1/2216* (2013.01); *H01Q 5/40* (2015.01); *H01Q 7/00* (2013.01); *A61B 5/6852* (2013.01); *A61B 8/12* (2013.01); *A61B 2034/2051* (2016.02); *G06K 7/10316* (2013.01); *G06K 19/0672* (2013.01)

(58) Field of Classification Search
CPC ....... A61B 18/1492; A61B 8/12; A61B 18/24; A61B 5/6852; A61B 5/0084; A61B 8/445; A61B 2034/2051; A61B 2018/1861; A61B 90/98; A61B 2560/0219; G06K 19/07767; G06K 19/0723–0727; G06K 19/07773–07794; G06K 19/0672
See application file for complete search history.

(56) References Cited

U.S. PATENT DOCUMENTS

| | | | | |
|---|---|---|---|---|
| 7,806,333 | B1* | 10/2010 | McReynolds | G06K 7/0008 235/449 |
| 8,847,434 | B2* | 9/2014 | Hennig | A61B 5/0031 307/104 |
| 9,498,647 | B2* | 11/2016 | Kantrowitz | A61N 5/1049 |
| 2003/0120150 | A1* | 6/2003 | Govari | A61B 5/0031 600/424 |
| 2005/0099290 | A1* | 5/2005 | Govari | A61B 5/06 340/539.13 |
| 2006/0267759 | A1* | 11/2006 | Levine | A61B 5/06 340/539.12 |
| 2008/0086046 | A1* | 4/2008 | Petcavich | A61B 5/06 600/373 |
| 2010/0321246 | A1* | 12/2010 | Troesken | G01S 13/878 342/463 |
| 2011/0163857 | A1* | 7/2011 | August | G06K 19/0707 340/10.42 |
| 2012/0249396 | A1* | 10/2012 | Parsche | H01Q 1/243 343/866 |
| 2014/0028327 | A1* | 1/2014 | Potyrailo | G01R 35/005 324/601 |
| 2014/0030986 | A1* | 1/2014 | Caruana | H04B 7/028 455/75 |

FOREIGN PATENT DOCUMENTS

| | | |
|---|---|---|
| EP | 0257688 | 1/1991 |
| WO | WO2005067563 | 7/2005 |

* cited by examiner

SYSTEM FOR LOCATING AN OBJECT USING AN ANTENNA ARRAY WITH PARTIALLY OVERLAPPING COILS

CROSS-REFERENCE TO RELATED APPLICATIONS

This application is a 371 of PCT application PCT/EP2014/074461 filed on Nov. 13, 2014. PCT/EP2014/074461 filed on Nov. 13, 2014 claims the benefit of U.S. Provisional application 61/904,111 filed on Nov. 14, 2013.

FIELD OF THE INVENTION

This invention relates to sensing and detecting systems. In particular, the invention relates to systems for detecting medical instruments.

BACKGROUND OF THE INVENTION

Tubes and catheters are inserted in critically ill and fragile patients, which differ in age from new-borns till elders who need feeding or breathing support. The tube or catheter is inserted with a lifesaving or supporting goal and is a precise and accurate procedure. Most of the time the patients cannot give any feedback due to very young age or comatose state and therefore for the catheter to reach its desired position and location is mainly dependent on the expertise of medical personal. With medical procedures, such as aspiration, auscultation, radiography (x-ray), or pH testing, there is no guarantee that the catheter is placed correctly. These procedures differ in complexity; time needed to complete, costs and considered health risk for the patient. The worst scenario of misplacement could actually result in death of the patient.

Accordingly, the technical challenges of existing medical procedures are posed especially on reliability, safety, costs and usability seen the environment it has to be used in. The need for technology that aids clinical personnel in determining the position of a tube or catheter and avoiding misinterpretations of the actual situation is evident.

SUMMARY OF THE INVENTION

A system for wirelessly locating an object is provided. A passive electromagnetic reflector can be (removably) affixed to an object that one desires to track or locate. The passive electromagnetic reflector has a coil configured to: (i) receive a signal of frequency $f_0$, and (ii) selectively reflects multiples of $f_0$. A transceiver unit has an antenna array with two partially overlapping coils. The first coil is tuned to transmit the signal of frequency $f_0$ to be received by the passive electromagnetic reflector. The second coil is tuned to receive the non-linear multiples of $f_0$ reflected by the passive electromagnetic reflector. The overlap is defined such that the distance d between the centers of the first and the second coils depends on the radius r of the first coil according to: $d=(2 \times r)/1.503(\pm 0.07)$. The first and second coils are at least planar for the area where they overlap. The overlapping coils cause a change in field distribution so that the intrinsic pattern is partially inverted in respect to the electromagnetic reflector. The inverted pattern leads to a small focus area at the front and back of the coil configuration.

Embodiments of the invention have the following advantages. First, the operation of the system is not influenced by the human composition or by the environment. Second, the electromagnetic reflector is detectable in a highly electromagnetic reflective environment and when situated on an electromagnetic reflective surface. Third, the overlapping coils provide the system with a large dynamic range for multiple $f_0$ to achieve enough measurement distance to detect the electromagnetic reflector inside a human body of different sizes with a minimum amount of RF (electromagnetic) power. Fourth, the inverted intrinsic pattern of the coils focuses the field distribution with respect to the electromagnetic reflector over a small area, which contributes to the efficiency of the link between scanner and electromagnetic reflector and leads to an accurate detection of the electromagnetic reflector in the x- and y-plane in the scan direction.

DETAILED DESCRIPTION

The invention is a system for wirelessly locating an object, especially objects that are hidden from direct visual inspection. In a specific embodiment the object to be located is a tip of a nasogastric feeding tube that is inserted in a human body. However, the invention is not limited to various medical applications and can also be useful in any other situation where a hidden object needs to be located or tracked. The system contains a transducer or electromagnetic (EM) reflector 100 and a scanner or transceiver unit 200 as shown in respectively FIGS. 1-2. In one variation the scanner can be equipped with sensors, such as an accelerometer to keep track of the direction of movement.

Reflector

Figure 1:
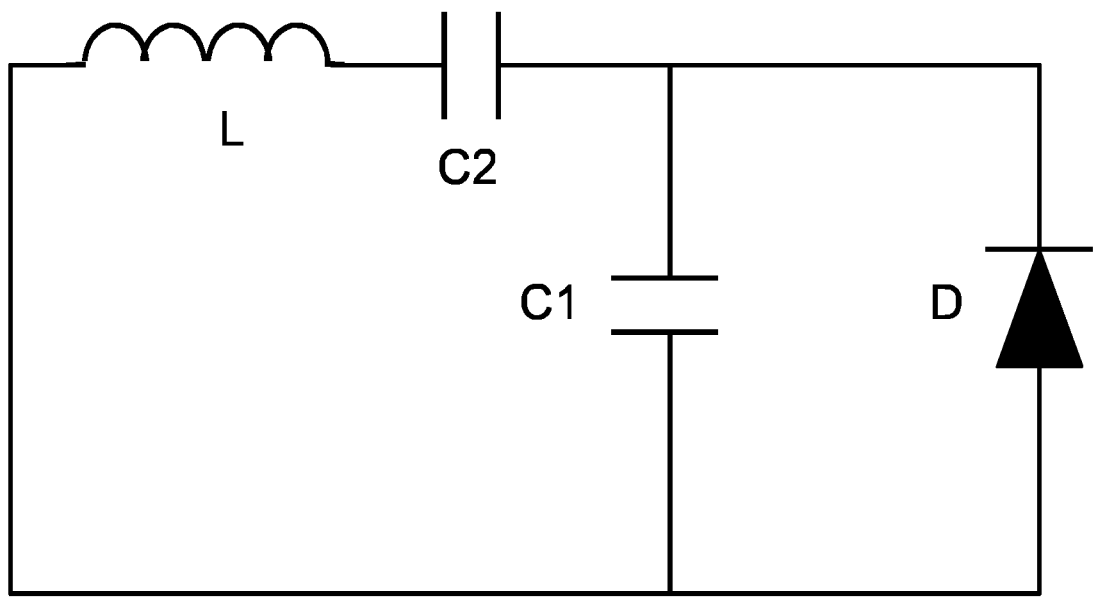
FIG. 1 shows a transducer or electromagnetic (EM) reflector 100 according to an exemplary embodiment of the invention.
Figure 2:
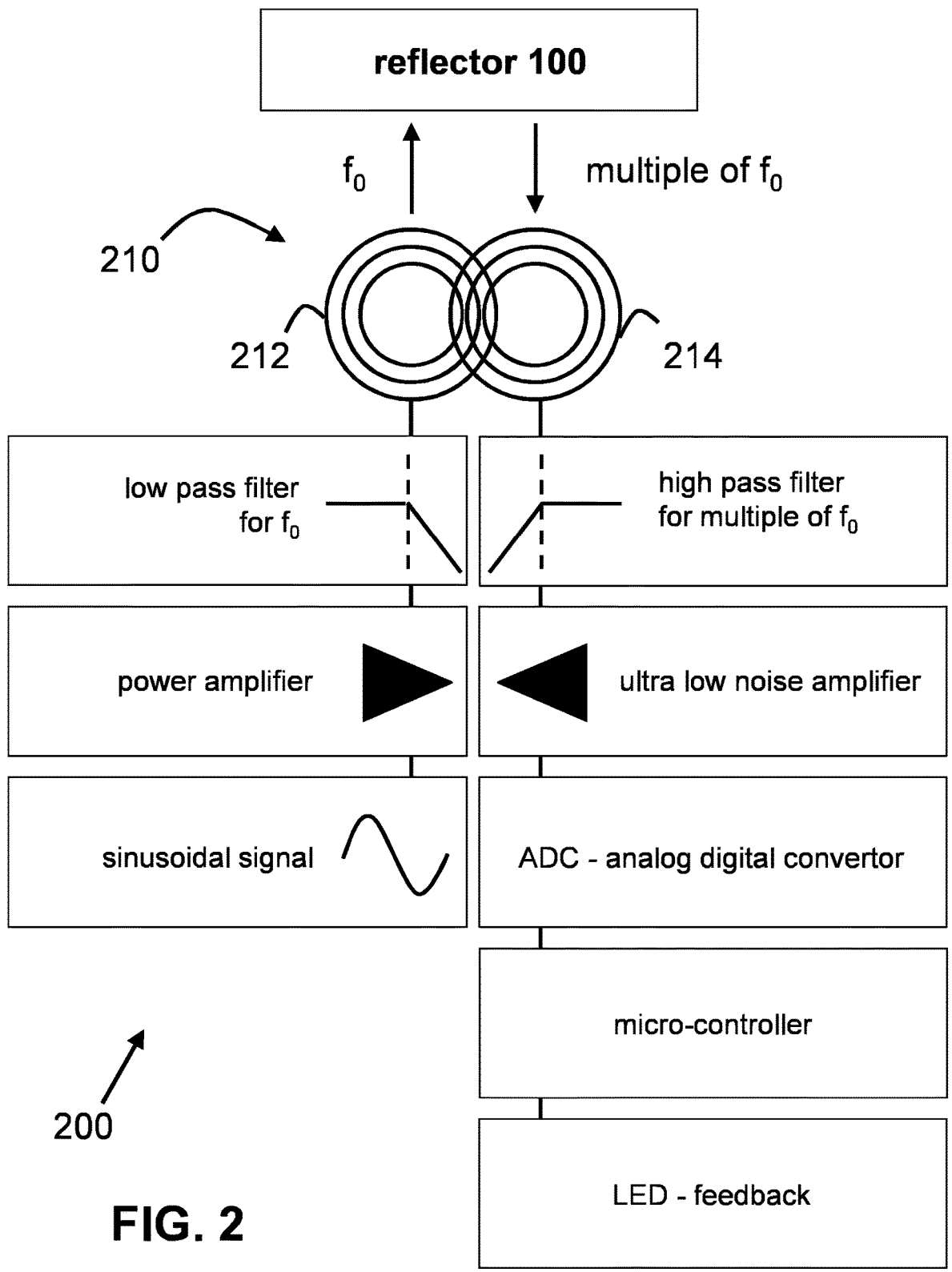
FIG. 2 shows a scanner or transceiver unit 200 in combination with reflector 100 according to an exemplary embodiment of the invention.

Transducer or electromagnetic (EM) reflector 100 is a passive (i.e. wirelessly powered) electromagnetic reflector that can be affixed to an object that one desires to locate. The electromagnetic reflector contains a ferrite antenna (coil) L with a diode D and a series C2 and parallel C1 capacitor (FIG. 1). Reflector 100 is tuned to receive a signal with a frequency $f_0$ and will reflect higher multiples of $f_0$ (e.g. second or third harmonics of $f_0$) caused by the nonlinear effects of the diode D (FIG. 2). The combination of capacitors, C1 and C2, will tune the reflector 100 to be susceptive to the desired frequencies and will lower the threshold voltage of the diode D for $f_0$.

The size of reflector 100 is mainly determined by coil L. For the medical application of locating the tip of a nasogastric feeding tube, the reflector could differ from 1.2 mm×5.0 mm for children and neonates to 3.0 mm×25.0 mm for adults. The coil L is designed for frequencies from 100 kHz to 500 kHz with a bandwidth of 30% in respect to the center frequency for transmitting as receiving the signal.

The values of the capacitors C1 or C2 are configured to create a resonant circuit adapted to the first harmonic ($f_0$) as well as the higher harmonics (non-linear multiples of $f_0$) to improve the quality factor of the circuit between 40 and 80%. The setup could be a combination of C1 and C2 or just one of both added to the design.

Diode D can be a RF Schottky with a low threshold value of 240 mV or lower. The function of diode D is twofold. The first function of D is to backscatter the signal of any frequency. The second function of D is to create higher harmonics than $f_0$. With the function of creating higher harmonics reflector 100 becomes a source of unique frequency and the only source transmitting (i.e. reflecting) that specific higher frequency.

In one example, the reflector can be characterized with L being a ferrite antenna coil with an inductance of about 250 nH, C1 and C2 being ceramic capacitors with values chosen to create a resonant circuit, D having a threshold voltage as low as possible and suitable for frequencies starting from 100 kHz. In terms of sizing, the reflector needs to be able to be inserted in e.g. a feeding tube sized for preterm born babies with dimension of 1 mm×5 mm (width×length).

Scanner/Transceiver Unit

As shown in FIG. 2, the transceiver unit 200 has an antenna array 210 with two partially overlapping coils, 212, 214. The first coil is tuned to transmit the signal of frequency $f_0$ to be received by the passive electromagnetic reflector 100. The second coil is tuned to receive the non-linear multiples of $f_0$ (e.g. $2^{nd}$ or $3^{rd}$ harmonics) reflected by the passive electromagnetic reflector 100.

The sinusoidal signal is created with the aid of an electronic oscillator circuit. Depending on the composition of this circuit a low pass filter is required to avoid higher harmonics originated from electronic oscillator circuit. The signal will be amplified to achieve a certain distance where the power is limited to mandatory levels. The electronic oscillating circuit can perform a frequency sweep to allow the circuit to find the ideal frequency for maximum signal strength with minimum amount of power. The transmit coil, tuneable to a specific resonance frequency adapted to the electromagnetic reflector, will emit the power into the environment. With enough power, which is related to the distance between the scanner and electromagnetic reflector, the electromagnetic reflector will wake up and reflects back multiples of $f_0$. Multiples of $f_0$. The arrangement of coils is such that they are separated galvanic as RF which means that the signal coupling is brought back to an absolute minimum.

The received signal from reflector 100 is filtered and amplified to minimize the contribution of $f_0$. A high pass filter is used to filter the multiple frequencies of $f_0$, e.g. 2nd or $3^{rd}$ harmonics of $f_0$. Because the signal detected is of very low energy an ultra-low noise amplifier is used to assure a minimum contribution of noise from the amplifier to the system and assure enough signal to noise ratio or signal quality to be detected. The filtered and amplified signal is then passed through an Analog to Digital Converter (ADC). The digital values are processed with use of a microcontroller to detect for example the relative maximum received power from reflector 100. To aid in determining the exact location an LED light system can be used on the scanner. The LED could turn red when the system is active but no reflector is detected, orange when a minimum threshold level is reached so the user knows it is in reach of the reflector and green after detecting the maximum peak power and the centre of the scanner head is directly on top of the reflector. While closing in on the reflector the color of the LED could slowly change until it is bright green to ensure an intuitive movement of the scanner towards the reflector.

Figure 3:
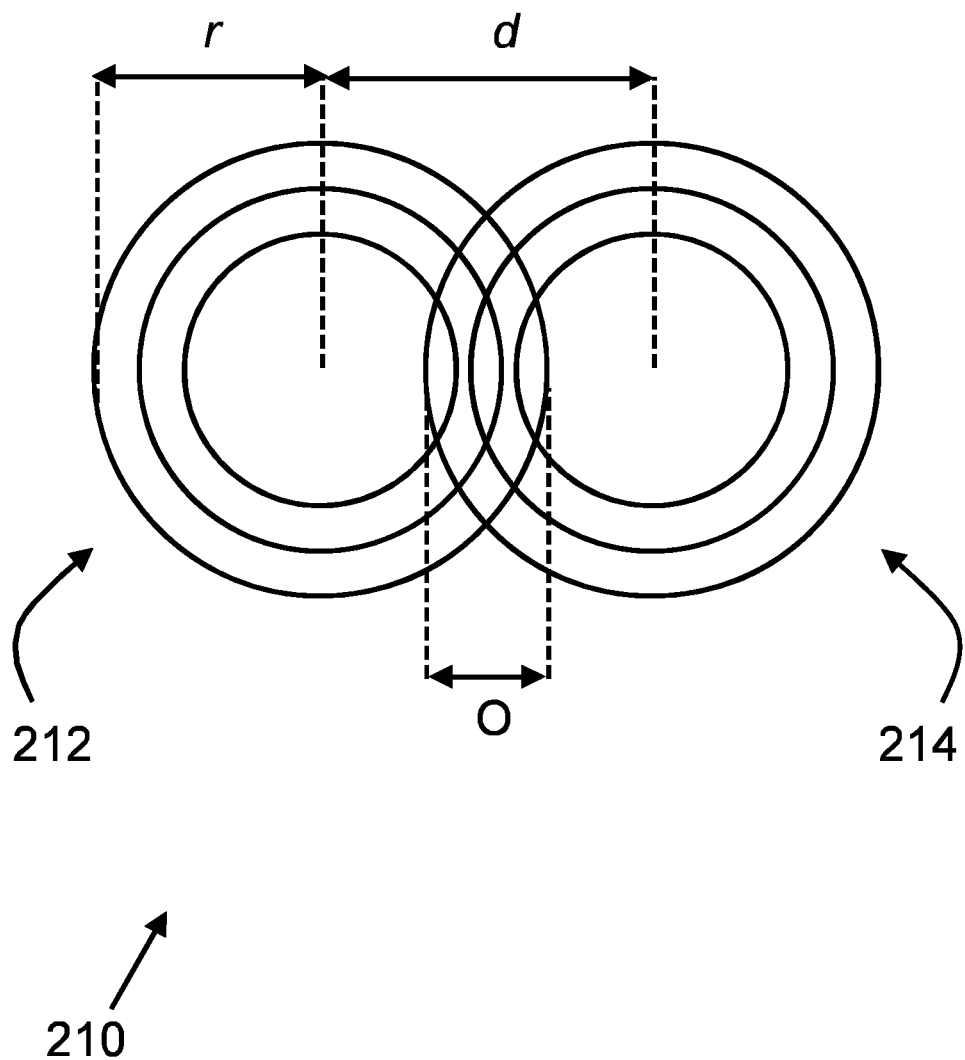
FIG. 3 shows a top view of two partially overlapping coils according to an exemplary embodiment of the invention.
Figure 4:
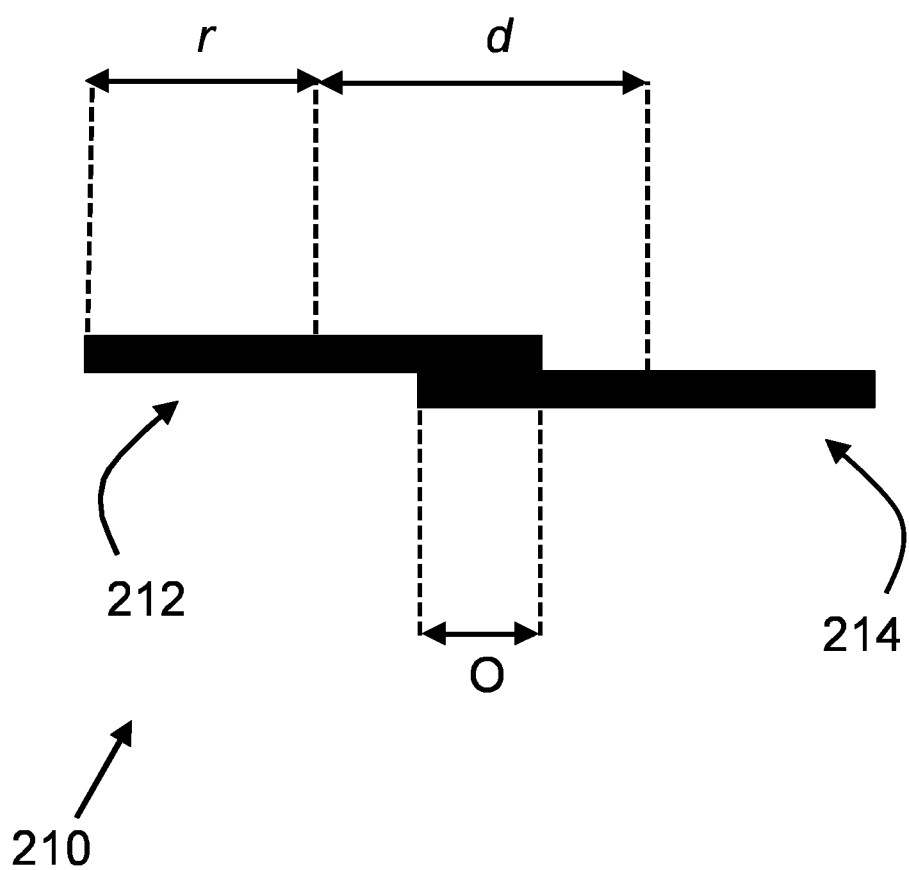
FIG. 4 shows a side view of two partially overlapping coils according to an exemplary embodiment of the invention.
Figure 5A:
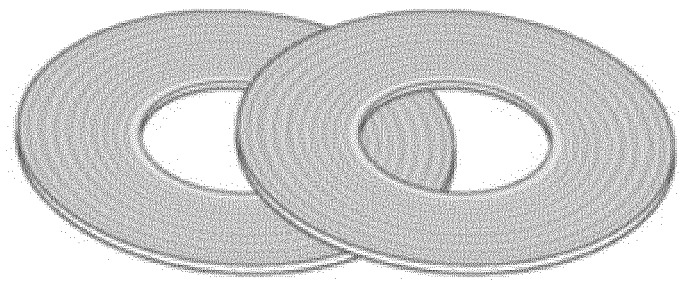
FIGS. 5A-C show according to exemplary embodiments of the invention different coil configurations to show that the antenna array can become conformal without disturbing the field distribution and without disturbing the coil coupling. Small configurations are beneficial for integrating into a small device when used for preterm born babies.
Figure 5B:
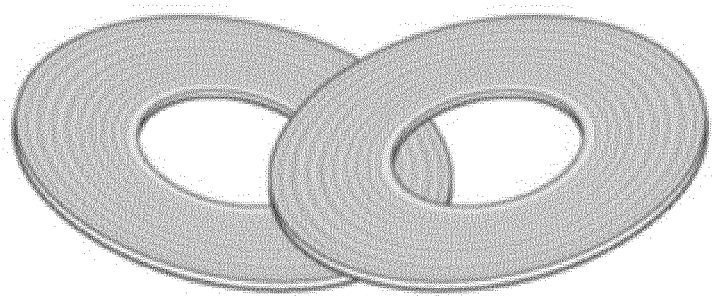
Figure 5C:
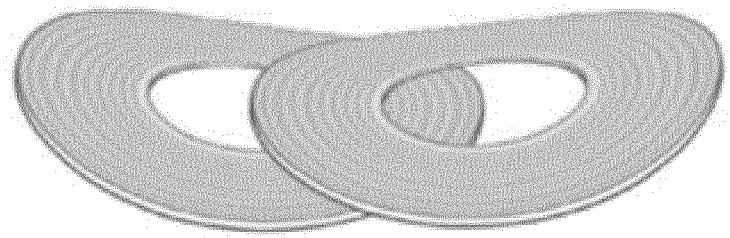

FIGS. 2-4 shows two partially overlapping coils 212, 214. The overlap area O is defined such that the distance d between the centers of the first and the second coils depends on the radius r of the first coil according to:

$$d=(2\times r)/1.503 (\pm 0.07)$$

For example, if r=21 mm, d is 27.94 mm. Radius r is defined with a tolerance of 4% as the coil might differ due to production tolerances. This overlap equation holds true for circular shaped coils, but also for non-circular shaped coils (e.g. elliptical, square, rectangular, etc.). The coils could be planar, but don't have to be completely planar. The only aspect that needs to be planar is the overlapping parts of the coils. The coils are aligned in such a way that the power field distribution is focused to a small area around the two points where the outer diameters of the coils meet, i.e. the intrinsic pattern of the coil is inversed and bend in an arc with a specific radius to amplify the focused area.

In one example the coil can be characterized as being planar with an inductance of about 48 µH for the transmit coil and about 24 µH for the receiver coil. The coils can be made of Litze wire to reduce the skin effect and improve efficiency and are electrically isolated from each other. The transmit and receive coils could have a combined diameter of about 60 mm, while the transponder is just 8 mm by 2 mm. A readout distance of 50 mm with 20 mW output power can be achieved. The alignment of the coils must be accurate within 1 mm to achieve an attenuation of approx. 70 dB of the coupled multiples frequencies of $f_0$.

The invention claimed is:

1. A system for wirelessly locating a tip of a medical tube or catheter inserted in a human body, comprising:
   (a) a passive electromagnetic reflector affixed to the tip of the medical tube or the catheter, wherein the passive electromagnetic reflector has a coil configured to: (i) receive a signal of frequency $f_0$, and (ii) selectively reflect multiples of $f_0$; and
   (b) a transceiver unit having an antenna array with two partially overlapping coils, wherein the overlap is defined such that the distance d between the centers of the first and the second coils depends on the radius r of the first coil according to: $d=(2\times r)/1.503$ ($\pm 0.07$), wherein (j) the first coil is tuned to transmit the signal of frequency $f_0$ to be received by the passive electromagnetic reflector, and (jj) the second coil is tuned to receive the multiples of $f_0$ reflected by the passive electromagnetic reflector.

2. The system as set forth in claim 1, wherein the first and second coils are planar for the area where they overlap.

3. The system as set forth in claim 1, wherein $f_0$ has a frequency between 100 kHz and 150 kHz.

4. The system as set forth in claim 1, wherein the transceiver unit comprises an LED lighting system that is configured to adjust a color of its light emission in dependence of a received power from the passive electromagnetic reflector.

5. The system as set forth in claim 1, wherein the antenna array is conformal.

* * * * *